United States Patent [19]

Selwyn

[11] 4,302,439
[45] Nov. 24, 1981

[54] METHOD OF DISCLOSING DENTAL PLAQUE WITH D AND C RED 33

[76] Inventor: Stephen L. Selwyn, 18 Franklin Close, Whetstone, London, N2O 9QG, England

[21] Appl. No.: 169,489

[22] Filed: Jul. 16, 1980

Related U.S. Application Data

[63] Continuation of Ser. No. 37,757, May 10, 1979, abandoned, which is a continuation of Ser. No. 783,444, Mar. 31, 1977, abandoned.

[30] Foreign Application Priority Data

Apr. 7, 1976 [GB] United Kingdom ............... 14189/76

[51] Int. Cl.³ .................. A61K 6/00; G01N 1/30; G01N 33/48
[52] U.S. Cl. .......................... 424/7; 424/3; 424/49
[58] Field of Search ................. 424/3, 7, 49

[56] References Cited

U.S. PATENT DOCUMENTS 3,159,316 12/1964 O'Donnell .
3,309,274 3/1967 Brilliant ................................. 424/7
3,624,219 11/1971 Perlitsh ................................. 424/7
3,723,613 3/1973 Block .................................... 424/7
3,903,252 9/1975 Stearns ................................. 424/7

FOREIGN PATENT DOCUMENTS 2203618 5/1974 France ................................. 424/7
51-38427 3/1976 Japan ................................... 424/7

OTHER PUBLICATIONS

Balsam & Sagarin, Cos Sci & Tech., Wiley-Intersci., Pub. NY, vol. I, 1972, pp. 428-433, 474, 475, 496-499, 508-509, 540-541, 546-549; vol. III, 1973, pp. 548-550, 563-565.
Color Index, The Soc. of Dyers & Colourists, Eng. & Amer. Asso. of Textile Chem. & Colorists, 3rd Ed., 1971, pp. 1134, 2773, 2783, 2785, 5015.

Primary Examiner—Anna P. Fagelson
Attorney, Agent, or Firm—Browdy and Neimark

[57] ABSTRACT

The dye D and C Red 33 is used as dental plaque disclosing agent, inter alia having the form of a mouthwash, gel or tablet.

8 Claims, No Drawings

METHOD OF DISCLOSING DENTAL PLAQUE WITH D AND C RED 33

This is a continuation of application Ser. No. 37,757 filed, May 10, 1979 which in turn is continuation application of Ser. No. 783,444, filed Mar. 31, 1977, both abandoned.

This invention relates to dental plaque disclosing agents.

Dental plaque is the name applied to a bacterial film which forms on teeth and causes dental disease. Dental plaque is normally difficult to see. The presence of dental plaque can be shown by means of dental plaque disclosing agents which are applied to the teeth and colour the dental plaque. The location of areas of dental plaque is desirable, of course, because the dental plaque can then be removed from teeth for example by a dentist in his surgery or by an individual at home.

According to the present invention there is provided a process for disclosing dental plaque on the teeth of an individual which comprises the individual taking into his or her mouth and applying to the teeth the dye D and C Red 33 which stains any dental plaque on the teeth.

The dye D and C Red 33 is also known as Red 10B, C.I. Acid Red 33 and Food Red 12. It is an azo dye made by coupling aniline and H-acid(8-amino-1-naphthol-3,6-disulphonic acid).

The dye is taken into the mouth of an individual whose teeth are to be examined for dental plaque and stains the dental plaque a red colour so that the plaque is readily visible. The stain on the dental plaque caused by the dye will persist and is not readily removed from the dental plaque by, for example, rinsing of the mouth. However, any stain on soft oral tissue in the mouth which is caused by the dye will not persist. Thus an individual to whom dye is applied is not left with a persistent objectionable coloured stain on the soft oral tissues. Persistent objectionable stains have discouraged individuals and dentists from using plaque disclosing agents. Furthermore, the dye does not require the use of special light, for example, ultra-violet light to render dental plaque apparent.

D and C Red 33 can be applied in any suitable form, for example as a tablet or pastil, in gel form, on swabs or in solution, preferably in water.

In a preferred method of application, D and C Red 33 in solution in water is contained in a vessel provided with actuating means such as a small pump designed to expel from the vessel a metered dose of solution when a push button is depressed. Preferably the vessel is provided with a tube through which the solution is expelled and this tube is placed behind the lower front teeth when the solution is applied. The concentration of D and C Red 33 in water can vary between wide ranges but concentrations in the range of from 1.0 to 6.0% weight by volume are found satisfactory. When using a metering pump which dispenses 0.7 to 0.8 mls in one dose it is preferred to use a solution whose concentration is 3.5% weight by volume.

A suitable dispenser by means of which the solution can be expelled is that described in U.S. Pat. No. 3,159,316.

D and C Red 33 is stable to heat and light under ambient conditions and can therefore be kept in, say, a bathroom for normal daily use by an individual. If necessary, however, stabilising agents, for example Nipasept, Nipabutyl, sodium benzoate, benzoic acid or sulphur dioxide can be incorporated with the D and C Red 33. Fluorides to strenghten teeth against decay, and tooth cleaning agents can also be incorporated.

D and C Red 33 has no objectionable flavour and is therefore particularly suitable for application in solution in the form of a mouthwash. If desired, flavouring agents can be incorporated in the solution. Preferred compositions suitable for use as a mouthwash comprise D and C Red 33, Anise oil, peppermint oil, ethyl alcohol and/or propylene glycol and a preserving agent in solution in deionised water.

The ethyl alcohol and/or propylene glycol act as solubilising agent for the peppermint oil, which is a flavouring agent.

The preserving agent may be Nipasept, a mixture of the methyl, ethyl and propyl esters of parahydroxybenzoic acid, or Nipabutyl, butylhydroxybenzoate, or preferably a mixture of these two agents.

EXAMPLE

An example of such a preferred mouthwash is set out below:
(1) D and C Red 33—3.5 qm
(2) Propylene Glycol BP—7.5 ml
(3) Peppermint Oil BP—0.075 ml
(4) Nipasept 0.05 gm—Nipabutyl 0.0166 gm.
(5) Anise Oil—0.075 ml
(6) Deionised Water to 100 ml.

A gel composition can be formed by adding to the mouthwash composition a suitable thickening agent, for example a cellulose-derivative, such as sodium carbyxymethylcellulose, or a Carbomer (i.e., carboxypolymethylene or carboxyvinyl polymer).

An example of a preferred tablet composition is as follows:

D and C Red 33—37.5 mgs
Peppermint oil—1.0 mgs
Syloid 244—1.0 mgs
Sodium saccharin—0.6 mgs
Sodium bicarbonate—28.0 mgs
Mannitol USP granular—327.9 mgs
Calcium stearate—4.0 mgs An absorbent material for the peppermint oil. Syloid 244 is marketed by W. R. Grace and Company.

A test was carried out in which forty individuals were asked to use a plaque disclosing agent and then to clean their teeth. Each individual was asked to decide when he considered that the staining of his lips and gums caused by the plaque disclosing agent had disappeared. The plaque disclosing agent were the preferred mouthwash in accordance with this invention, whose composition is given above, and a 2% wt/volume solution in water of erythrosine, erythrosine being a known plaque disclosing agent. All forty individuals found that after using the mouthwash of this invention there was minimal staining of lips and gums two minutes after cleaning teeth. After using erythrosine objectionable staining of lips and gums persisted for a much longer period, often for many hours. Moreover unlike with erythrosine, and many other disclosing agents, any skin staining can be readily washed off after using D and C Red 33.

I claim:

1. A method for disclosing dental plaque which comprises administering a plaque-disclosing amount of the dye D and C Red 33, having the formula

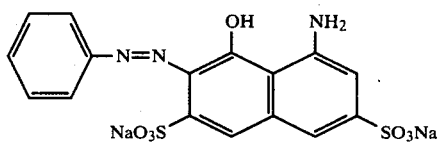

to an individual to stain any dental plaque on the teeth of said individual.

2. A process according to claim 1, wherein said dye D and C Red 33 is administered into the mouth in the form of a tablet, a pastil, in gel form, on swabs or in solution in water.

3. A method in accordance with claim 1 wherein said dye D and C Red 33 is administered in the form of a solution comprising said dye, a flavoring agent, an alcohol selected from the group consisting of ethyl alcohol, propylene glycol and mixtures thereof, and a preserving agent in deionized water.

4. A method in accordance with claim 3, wherein said preserving agent is a mixture of the methyl, ethyl and propyl esters of parahydroxybenzoic acid.

5. A method in accordance with claim 3, wherein said preserving agent is butylhydroxybenzoate.

6. A method in accordance with claim 3, wherein said preserving agent comprises a mixture of the methyl, ethyl and propyl esters of parahydroxybenzoic acid and butylhydroxybenzoate.

7. A method in accordance with claim 1 wherein said dye D and C Red 33 is administered into the mouth in the form of a tablet.

8. A method in accordance with claim 7, wherein said tablet comprises a flavoring agent, sodium saccharin, sodium bicarbonate, mannitol and calcium stearate.

* * * * *